(12) United States Patent
Doverbo et al.

(10) Patent No.: US 7,413,789 B2
(45) Date of Patent: Aug. 19, 2008

(54) ABSORBENT STRUCTURE AND A METHOD FOR MANUFACTURING AN ABSORBENT STRUCTURE

(75) Inventors: Anna-Gerd Doverbo, Molndal (SE); Ingemar Fernfors, Molndal (SE)

(73) Assignee: SCA Hygiene Products, Goteborg (SE)

( * ) Notice: Subject to any disclaimer, the term of this patent is extended or adjusted under 35 U.S.C. 154(b) by 378 days.

(21) Appl. No.: 11/013,418

(22) Filed: Dec. 17, 2004

(65) Prior Publication Data
US 2005/0137551 A1 Jun. 23, 2005

Related U.S. Application Data

(60) Provisional application No. 60/530,669, filed on Dec. 19, 2003.

(51) Int. Cl.
*B32B 3/24* (2006.01)
*A61F 13/15* (2006.01)
(52) U.S. Cl. .................. 428/136; 604/358; 604/384; 28/148; 229/120.36

(58) Field of Classification Search ............... 428/136; 28/148; 229/120.36; 604/358, 384
See application file for complete search history.

(56) References Cited

U.S. PATENT DOCUMENTS

| | | | |
|---|---|---|---|
| 2,402,709 A * | 6/1946 | Swasey | 28/148 |
| 3,150,693 A | 9/1964 | Seltzer | |
| 4,591,090 A * | 5/1986 | Collins et al. | 229/120.36 |
| 4,695,500 A | 9/1987 | Dyer et al. | |
| 4,746,053 A * | 5/1988 | Nichols | 229/120.36 |
| 4,795,083 A * | 1/1989 | Johnske | 229/120.36 |
| 5,883,022 A | 3/1999 | Elsener | |

FOREIGN PATENT DOCUMENTS

EP 1256331 A2 11/2002

* cited by examiner

*Primary Examiner*—William P Watkins, III
(74) *Attorney, Agent, or Firm*—Buchanan Ingersol & Rooney PC (57) ABSTRACT

An absorbent body includes a set of first strips and a set of second strips, wherein the first and second strips are coupled to each other in order to form an absorbent layer of the body. The first and second strips are coupled to each other by the first strips being provided with cuts in which the second strips are arranged.

35 Claims, 6 Drawing Sheets

ABSORBENT STRUCTURE AND A METHOD FOR MANUFACTURING AN ABSORBENT STRUCTURE

CROSS-REFERENCE TO RELATED APPLICATIONS

The present application claims the benefit of U.S. Provisional Application No. 60/530,669, filed in the United States on Dec. 19, 2003, the entire contents of which are hereby expressly incorporated herein by reference.

FIELD OF THE INVENTION

The present invention relates to an absorbent body and a method for manufacturing an absorbent body.

BACKGROUND OF THE INVENTION

Within a number of applications, there is a need of products which are capable of absorbing a fluid. One such application is hygiene products of different types, such as diapers, incontinence guards, pantyliners, etc., which should be provided with an absorbent body having the capacity of rapidly taking care of a relatively large fluid quantity. Thereby, the absorbent body should be capable of distributing the fluid and storing the fluid. Usually, two or more layers, which can be made of different kinds of material having different properties, are used in order to create such an absorbent body. At the same time, it is desired that the products are as thin as possible for a comfortable and discreet use. Accordingly, a compressed absorbent body having a small volume and a large absorption capacity is desirable. An absorbent body, or core, which is compressed too much and/or the use of rigid materials in the absorbent body, however, makes the product less flexible and ductile and, consequently, less comfortable to use.

Although the invention primarily is intended for providing the above-mentioned products, its should be emphasized that the invention also would be applicable to other similar products which are to possess the capacity of absorbing a fluid.

One type of textiles having absorption capacity are those manufactured by means of weaving. U.S. Pat. No. 4,695,500 describes such a woven structure intended for medical products, such as compresses, gauze bandages and the like. One property of woven or braided structures is that they are proportionately flexible and ductile even if they are made of a material which is rigid per se.

U.S. Pat. No. 5,883,022 describes how an absorbent textile is created by means of interweaving fibres, and especially how synthetic, continuous fibres are used in order to attain a high absorption capacity by means of alternatingly providing the textile fabric with regions where the fibres are bound to each other and with open regions where the fibres are non-bound to each other. The interstitial spaces of the textile fabric which are formed in this way enable fluid to be absorbed by means of the fluid being distributed and retained in the interstitial spaces through capillary action and adhesive forces.

In order to manufacture a woven textile, however, a complicated manufacturing method is required in which the threads, a warp and a weft, are interlaced. Due to its complexity, such a method would not be a realistic alternative to the present manufacturing methods for applications within the field of hygiene products. Production of hygiene products by means of weaving would not at all meet the demands upon production speed and cost efficiency which prevail when producing these products. Furthermore, when performing traditional weaving, it is required that the material parts which are interwoven, usually threads, have a sufficiently high strength, such as tensile strength, allowing them to be handled in the way required by the weaving process without being damaged. This means that many materials having a proportionately low strength, but which with regard to certain properties still could be suitable for use when forming an absorbent body, cannot be used when manufacturing a woven layer.

OBJECTS AND SUMMARY

It is an object of the invention to provide an absorbent body being proportionately flexible even if it is made of a proportionately rigid material.

A second object of the invention is to provide a method by means of which method a proportionately flexible absorbent body can be manufactured from a proportionately rigid material.

By means of using strips instead of a continuous layer, in accordance with an embodiment of the invention, a more open and flexible layer can be formed. As a result of said first and second strips being coupled to each other in such a way that said first strips are provided with cuts in which said second strips are arranged, the strips can be locked in relation to each other, at the same time as the layer can be designed so that the strips to a certain degree can be displaced in relation to each other in directions parallel to the formed layer. Furthermore, as a result of said second strips being arranged in the cuts of said first strips, the strips will locally be slightly curved, i.e. a pre-initiated bending or deformation is present in one or several positions, implying that the formed layer as a whole becomes more flexible.

An additional advantage is that such a layer exhibits a proportionately large exposed and to some extent irregular surface, creating the necessary conditions for a good absorption of a fluid. Furthermore, it is possible to design the absorbent body with apertures and/or cavities in order to increase its fluid acquisition capacity. Among other things, this implies that in case of the occurrence of a so-called gel-blocking, something which may occur for example in superabsorbent materials, such a fluid barrier will at worst be present in the respective strip, but not in the entire layer, something which could become the case if such a material were to be used in a traditional continuous layer.

Furthermore, the production of the absorbent body can be done in a rational and cost efficient way, also allowing the use of materials which could not be handled when utilising other manufacturing methods, such as weaving. The invention opens up for the creation of absorbent layers made of a number of material types and/or material combinations. For instance, the material in the above-mentioned second strips can be varied within one specific layer in order to give the layer different properties in different regions. Also the relative position of the strips in the layer can be varied, so that different properties are attained in different layers or within one specific layer. For instance, the layer can be given different density and/or absorption capacity in different regions.

An embodiment of the invention also relates to an absorbent product comprising a substantially fluid-impervious layer and a substantially fluid-pervious layer, said product having an absorbent body according to the invention arranged between the fluid-impervious layer and the fluid-pervious layer.

Other features and advantages of the invention are evident from the following description and the appended dependent claims.

BRIEF DESCRIPTION OF THE DRAWINGS

A detailed description of exemplifying embodiments of the invention, with reference the attached drawings, will follow below.

In the drawings:

FIG. 1b is an illustration of the opposite side of the layer according to an embodiment of the invention in FIG. 1a;

DETAILED DESCRIPTION OF PREFERRED EMBODIMENTS OF THE INVENTION

Figure 1A:
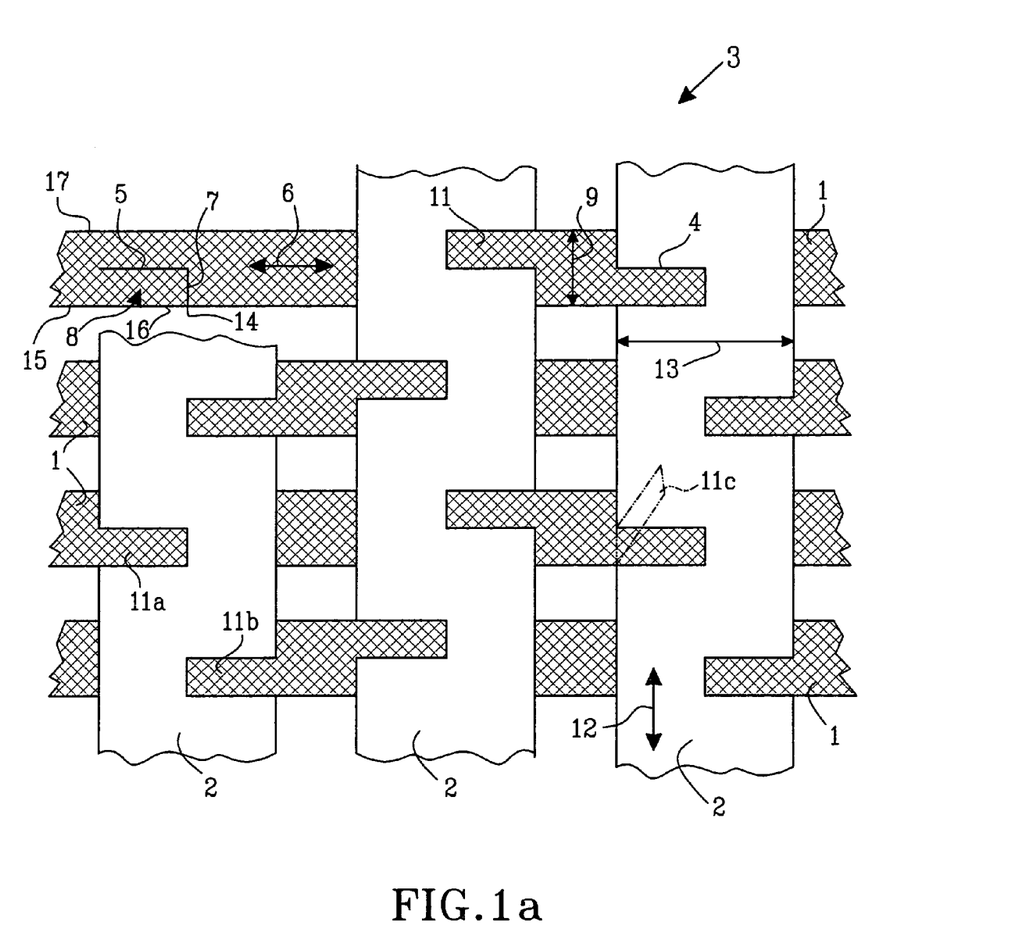
FIG. 1a is a schematic illustration of a first side of an absorbent layer according to an embodiment of the invention.
Figure 1B:
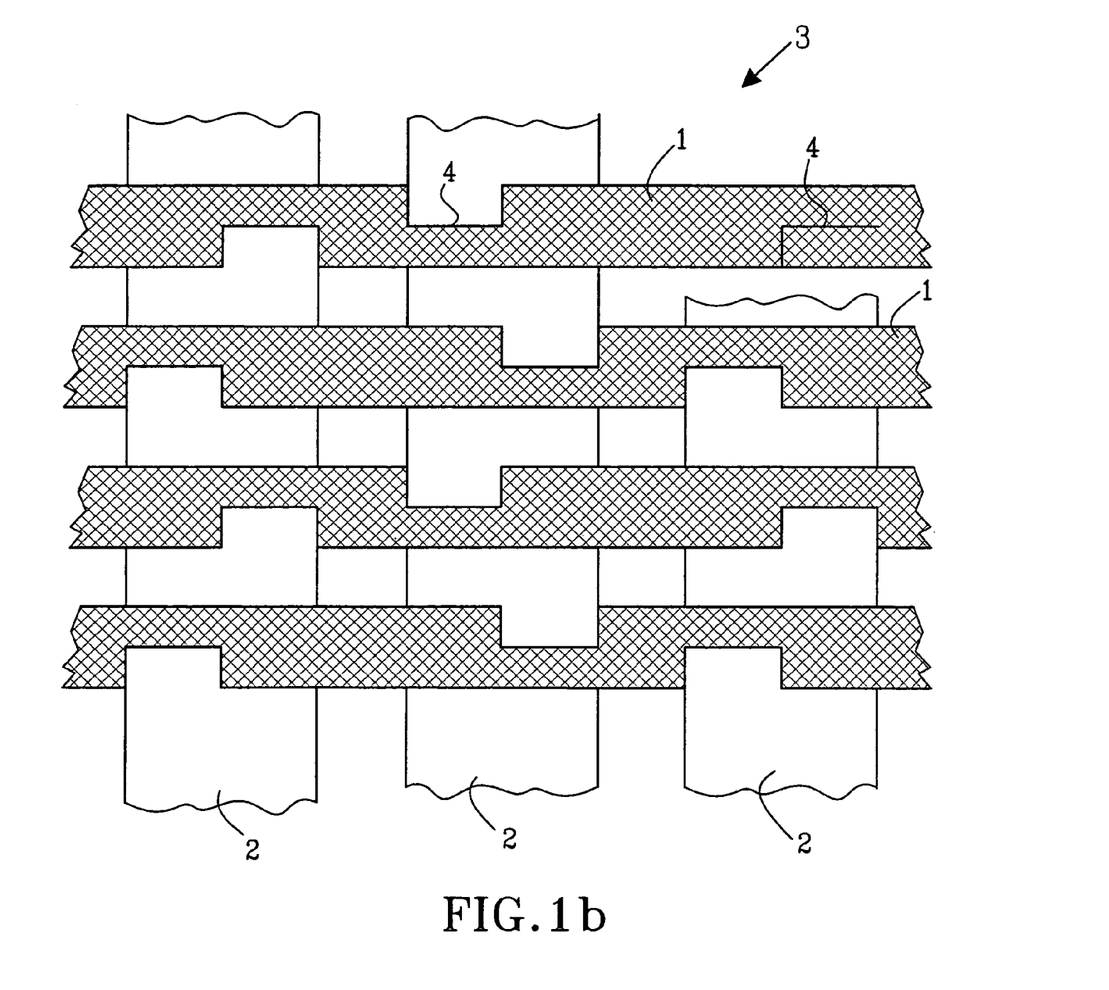

FIGS. 1a and 1b illustrate one embodiment of an absorbent body according to the invention. FIG. 1a shows a first side of the layer, and FIG. 1b shows the opposite side of the layer. The body comprises a set of first strips 1 and a set of second strips 2, wherein said first 1 and second 2 strips are coupled to each other in order form an absorbent layer 3 of the body. The first 1 and second 2 strips are coupled to each other by means of the first strips 1 being provided with cuts 4, in which cuts 4 the second strips 2 are arranged.

Although the illustrated embodiments of the invention include a plurality of the first strips and a plurality of the second strips, it is possible in other embodiments of the invention to form the absorbent layer from an arbitrary number of first and second strips. One, two or several of the first strips, which each can be provided with one, two or several of said cuts, can be coupled to one, two or several of the second strips. Accordingly, it should be emphasized that the expression "a set of first/second strips" means one, two or several such strips. Furthermore, the number of first strips can of course be different from the number of second strips. The layer preferably comprises two or several first strips, and preferably two or several second strips. In the most simple embodiment, however, the layer could be formed by a first strip being provided with a cut, and a second strip being arranged in the cut.

The cuts 4 can be said to have three main directions of extension, a first extension constituting the length of the cut, a second extension constituting the width of the cut and a third extension constituting the depth of the cut. As far as the depth of the cut is concerned, the cut suitably runs through the entire thickness of the respective first strip 1. The width of the cuts 4 is suitably as small as possible. (The material which, if necessary, still is removed when forming the cut is controlled by the properties of the tool being used for achieving the cuts.) Furthermore, the cuts 4 have an extension 5 in a longitudinal direction which is substantially parallel to the longitudinal direction 6 of said first strips 1 and an extension 7 in a longitudinal direction which is substantially perpendicular in relation to the longitudinal direction 6 of said first strips. In this way, the respective cut 4 obtains a substantially L-shaped 8 extension. The length of a cut 4 in the direction substantially perpendicular in relation to the longitudinal direction 6 of said first strips can correspond to approximately half the width 9 of one of said first strips 1. Furthermore, the length of said cut in the direction substantially in parallel with the longitudinal direction 6 of said first strips 1 can be of the same magnitude as the width 9 of one of said first strips 1.

In the illustrated embodiments, the first 1 and second strips 2 are arranged so that they cross each other. In another embodiment, however, the second strips could be arranged in parallel with the first strips. Thereby, the cuts of the first strips would exhibit an extension which is substantially perpendicular to the longitudinal direction of the first strips and the second strips.

However, an embodiment having strips laid crosswise is favourable for achieving a flexible structure. Suitably, the first strips 1 are arranged substantially in parallel with each other, and in a corresponding way the second strips 2 are arranged substantially in parallel with each other. Furthermore, the first 1 and second strips 2 can be arranged substantially perpendicularly in relation to each other.

Figure 2:
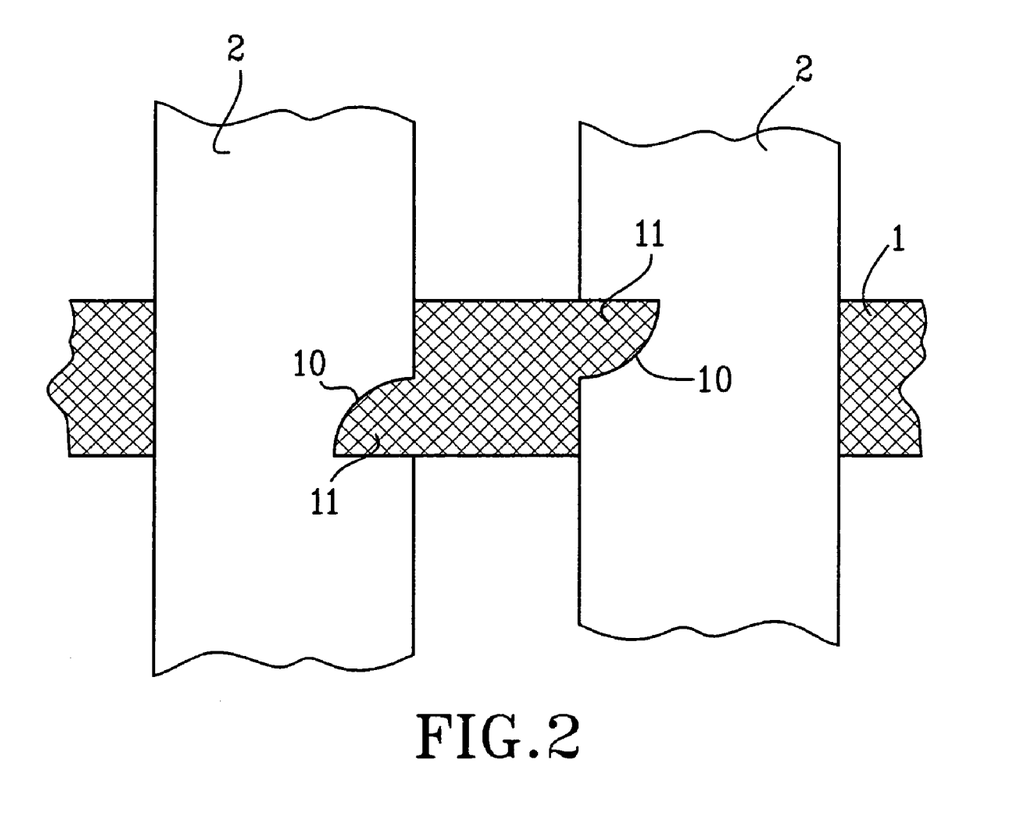
FIG. 2 is a cut according to an embodiment of the invention forming a variant of a flap of the layer.

Although the embodiment according to FIGS. 1a and 1b exhibits substantially L-shaped 8 cuts 4, it should be emphasized that the shape and dimensions of the cuts can be varied in a multitude of different ways within the scope of the invention. Examples of other possible designs is that the cuts have an extension 10 corresponding to a portion of circle, such as a semi-circle, or that the respective cut has an extension substantially corresponding to a quarter of a circle, as illustrated in FIG. 2.

In one advantageous embodiment of the invention, as illustrated in FIGS. 1a and 1b (and 3a and 3b), the cuts are arranged in order to form flaps 11 in said first strips. By means of designing the cuts 4 so that flaps 11, or tabs, are formed in the strips 1, a rational production of the absorbent body can be attained. The flaps 11 may be turnable up or down in relation to said respective first strip 1 for arranging one of said second strips 2 between the respective flap 11 and said first strip 1. When the flaps 11 are turned up, the second strips 2 can be placed on top of the first strips 1, whereupon the flaps 11 are turned down over the second strips 2. Along its extension in a longitudinal direction 12, the respective second strip 2 preferably is arranged between a plurality of flaps 11 and said first strips 1. Furthermore, FIG. 1a shows a schematic representation of how a flap 11c can be turned up.

The first 1 and second 2 strips can be coupled together by means of the cuts 4. By means of the cuts 4, the strips can be locked from lateral displacement in one or both directions. The length and position of the cuts 4 can be adapted to the width 13 of the second strips, so that a certain lateral displacement of the respective strip 2 can be allowed. In the embodiment according to FIG. 1, the flaps 11 are arranged for locking said second strip 2 in relation to said first strips 1 in a first direction being substantially parallel to the longitudinal direction 6 of said first strips, and in a second, opposite direction. The flaps 11 are arranged alternatingly on said first strips 1 so that, for a given flap 11a, said second strip 2 is locked in relation to said first strips 1 in a direction parallel to the longitudinal direction 6 of said first strips 1 and, by means of the closest adjacent flap 11b along said second strip 2, this is locked in the substantially opposite direction.

In the example illustrated in FIGS. 1a and 1b, the respective cut 4 is arranged for extending from a position 14 at one of the longitudinal side edges 15 of said respective first strip and further into the strip 1. Since a portion 16 of the periphery of the respective flap 11 is formed by a portion 16 of one of the longitudinal side edges 15 of the respective first strip 1, the total cut length which has to be achieved in order to create the flap 11 can be reduced in comparison with a case when the entire periphery of the flap 11 would be located inside the two side edges 15, 17 of the strip.

Figure 3A:
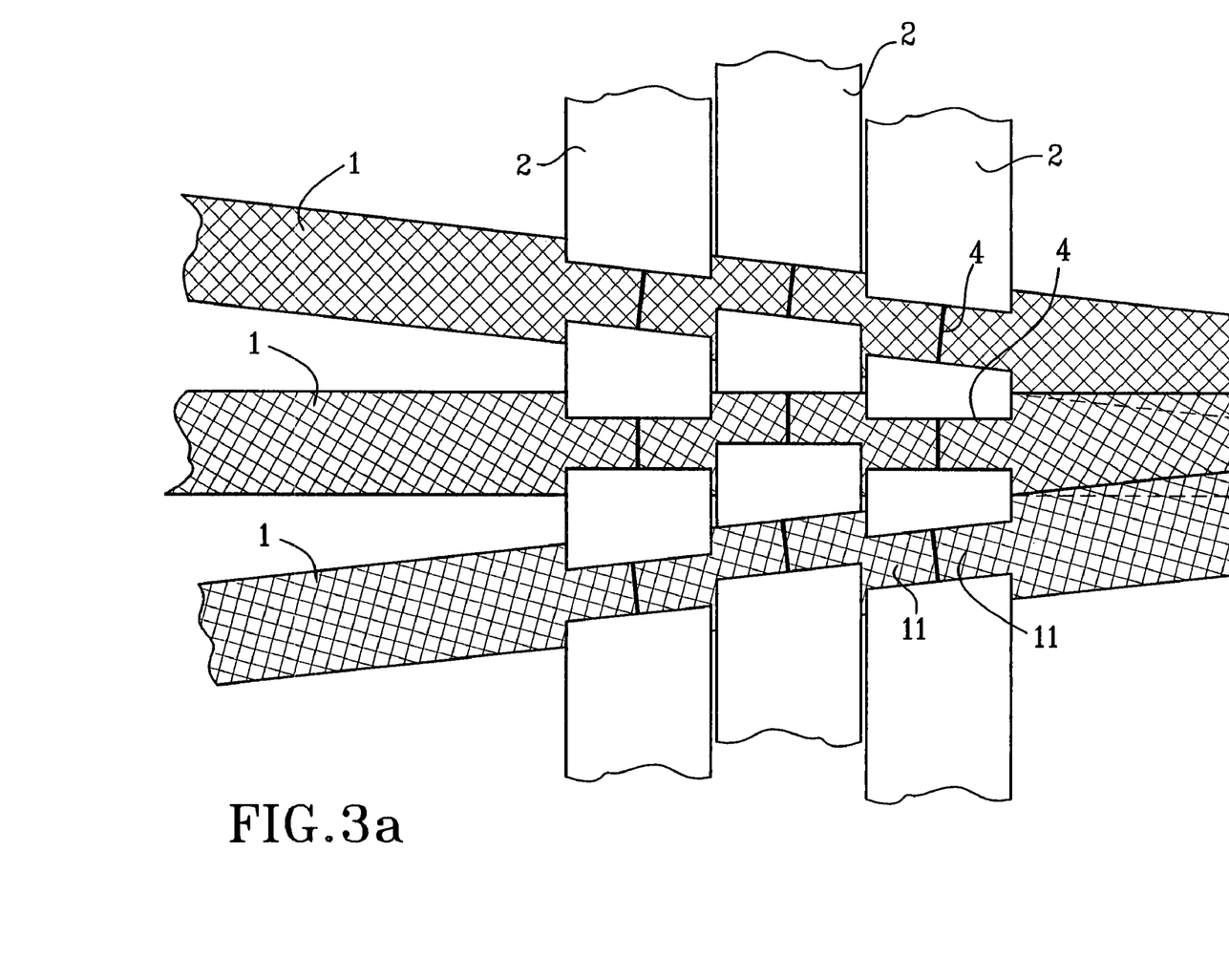
FIG. 3a is a schematic illustration of a first side of a variant of an absorbent layer according to an embodiment of the invention.
Figure 3B:
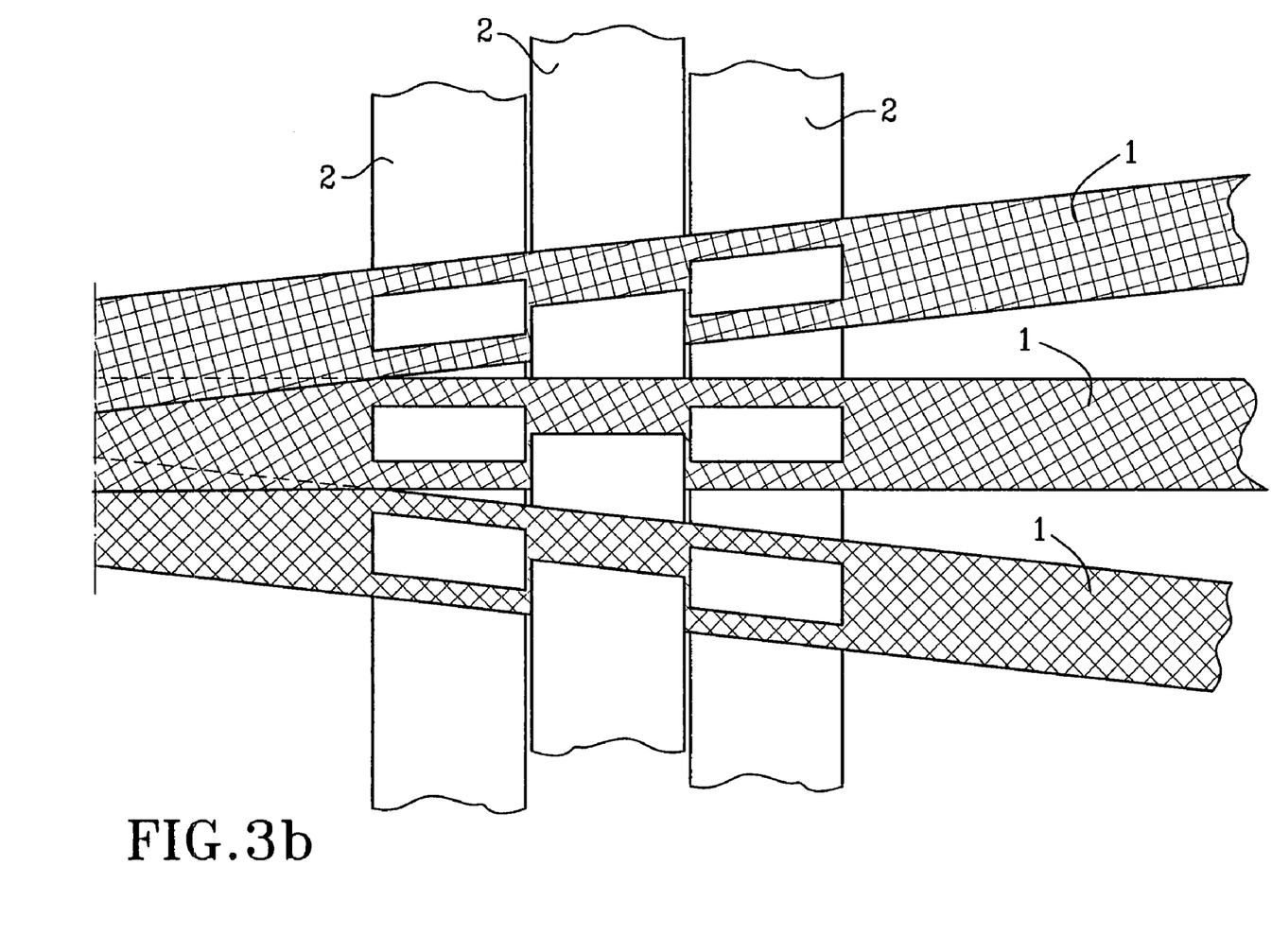
FIG. 3b is an illustration of the opposite side of the layer according to the embodiment in FIG. 3a, and FIG. 4 is a schematic illustration of a device for manufacturing an absorbent body according to an embodiment of the invention.

It is also possible to arrange the first strips 1 and/or the second strips 2 so that they partially overlap each other in a lateral direction, as shown in FIGS. 3a and 3b. FIG. 3a shows a first side of a variant of the layer 3, and FIG. 3b shows the opposite side of the layer 3. In one advantageous embodiment of the invention, the distance between the strips is varied, so that the strips are arranged more densely in certain regions of the formed absorbent layer 3. Due to the fact that the strips are arranged for overlapping each other, for example a structure which is suitable for a narrow crotch portion of a hygiene product exhibiting a so-called "boostered" absorption can be obtained. In FIGS. 3a and 3b, it is illustrated how the first strips 1 overlap each other in a lateral direction in order to form a more dense structure, but it is of course also possible to arrange the second strips 2 so that these overlap each other.

Of course, even if not illustrated, also the second strips could exhibit cuts for receiving said first strips in order to achieve an additional locking and coupling together of the strips.

In order to build up a thicker absorbent body and/or in order to attain other properties than those exhibited by a layer, the absorbent body can include two or several of said absorbent layers on top of each other. The layers, being arranged for overlapping each other, can be arranged in a substantially parallel disposition in relation to each other. In one embodiment, the absorbent layers are arranged alternatingly so that, for a given layer, the first strips have a longitudinal direction of extension which is substantially perpendicular to the direction of extension of the first strips in one of the closest adjacent layers. The first and second strips could be arranged in order to "change places" from one layer to the closest adjacent layer, i.e. when moving in the z-direction or, in other words, from one layer to another in the thickness direction of the layers, the next layer is turned approximately 90° in relation to the preceding layer.

The first strips 1 and the second strips 2 can exhibit a width 9, 13 within the interval from a few millimeters to about a hundred millimeters, preferably within the interval 5-100 mm, and usually within the interval 15-35 mm. The thickness of a strip can vary between one or a few tenths of a millimeter to tens of millimeters, preferably within the interval 0.1-10 mm. A strip of nonwoven material, for instance, can have a thickness which is about 0.5 mm, and a strip of cellulose pulp can have a thickness which is about 10 mm. The thickness and width of the strips 1, 2 are decided by the properties desired from the layer 3, and in dependence of which material the strips are made of. Both absorbent and non-absorbent materials are included amongst the materials which could be used. Examples of different materials are cellulose pulp, woven fabrics, nonwoven fabrics, fibrous materials, non-fibrous materials, foam materials, superabsorbent materials, synthetic materials such as thermoplastic fibres, and others.

The invention makes it possible for materials which are more rigid per se to form flexible products and, accordingly, more rigid materials are more preferred than soft materials, since soft or flexible materials can be used also in conventional structures. Examples of such more rigid materials are compressed materials, for example compressed cellulose pulp, such as, CP, TMP, CTMP, etc., compressed foam, compressed nonwoven or tissue laminates containing superabsorbents. Additional examples of rigid materials are materials in the form of a film, and especially different superabsorbents in the form of a film.

In one embodiment of the invention, the layer illustrated in FIG. 1a is formed by first strips made of cellulose pulp, either chemical pulp, CP, or such pulp blended with synthetic fibres so that the strips have a fibre content within the interval 2-15% by weight, preferably 10% by weight. The width of the strips is about 15 mm and the thickness is about 1-3 mm. The seconds strips are built up as laminates having an upper and a lower tissue layer, each with a thickness about 0.2 mm, and a layer of a superabsorbent arranged between the tissue layers, said superabsorbent layer having a thickness of about 1-3 mm. The width of the second strips is about 15 mm.

With regard to the dimensions and materials which can be used in order to create an absorbent body according to the invention, three examples of the first and second strips will follow below.

EXAMPLE 1

An above-mentioned first strip consists of 285 $g/m^2$ CP, 50 $g/m^2$ superabsorbent of a conventional type and 15 $g/m^2$ polypropylene. The components are blended and compressed, and are formed into a strip having 2 mm thickness and 15 mm width.

An above-mentioned second strip is a laminate and consists of 400 $g/m^2$ superabsorbent of a conventional type which is arranged between two tissue layers, 20 $g/m^2$ each. The strip is manufactured having a total thickness which is 1 mm and a width which is 15 mm.

EXAMPLE 2

An above-mentioned first strip consists of 125 $g/m^2$ CP and 50 $g/m^2$ superabsorbent of a conventional type. The components are blended and compressed, and are formed into a strip having 0.5 mm thickness and 15 mm width.

An above-mentioned second strip is a laminate and consists of 400 $g/m^2$ superabsorbent of a conventional type which is arranged between two tissue layers, 20 $g/m^2$ each. The strip is manufactured having a total thickness which is 1 mm and width which is 15 mm.

EXAMPLE 3

An above-mentioned first strip consists of 125 $g/m^2$ CP and 50 $g/m^2$ superabsorbent of a conventional type. The components are blended and compressed, and are formed into a strip having 1 mm thickness and 15 mm width.

An above-mentioned second strip consists of 175 $g/m^2$ CP, 70 $g/m^2$ superabsorbent of a conventional type. The components are blended and compressed, and are formed into a strip having 3 mm thickness and 15 mm width.

An embodiment according to the invention for manufacturing an absorbent body comprises the steps of coupling a set of first strips 1 and a set of second strips 2 to each other in order to form an absorbent layer 3 of the body and, furthermore, that the first 1 and second 2 strips are coupled to each other by means of providing the first strips with cuts 4, in which cuts 4 the second strips 2 are arranged. In one advantageous embodiment, the cuts 4 are designed so that flaps 11 which can be turned up and down in relation to the first strips 1 are formed in the first strips 1. The flaps 11 of the first strips 1 are turned aside and the second strips 2 are arranged on top of the first strips 1, whereupon the flaps 11 are turned back over the second strips 2. To this end, the first strips 1 can be provided with, for example, substantially L-shaped 8 cuts 4 or cuts having another suitable shape as described above.

Figure 4:
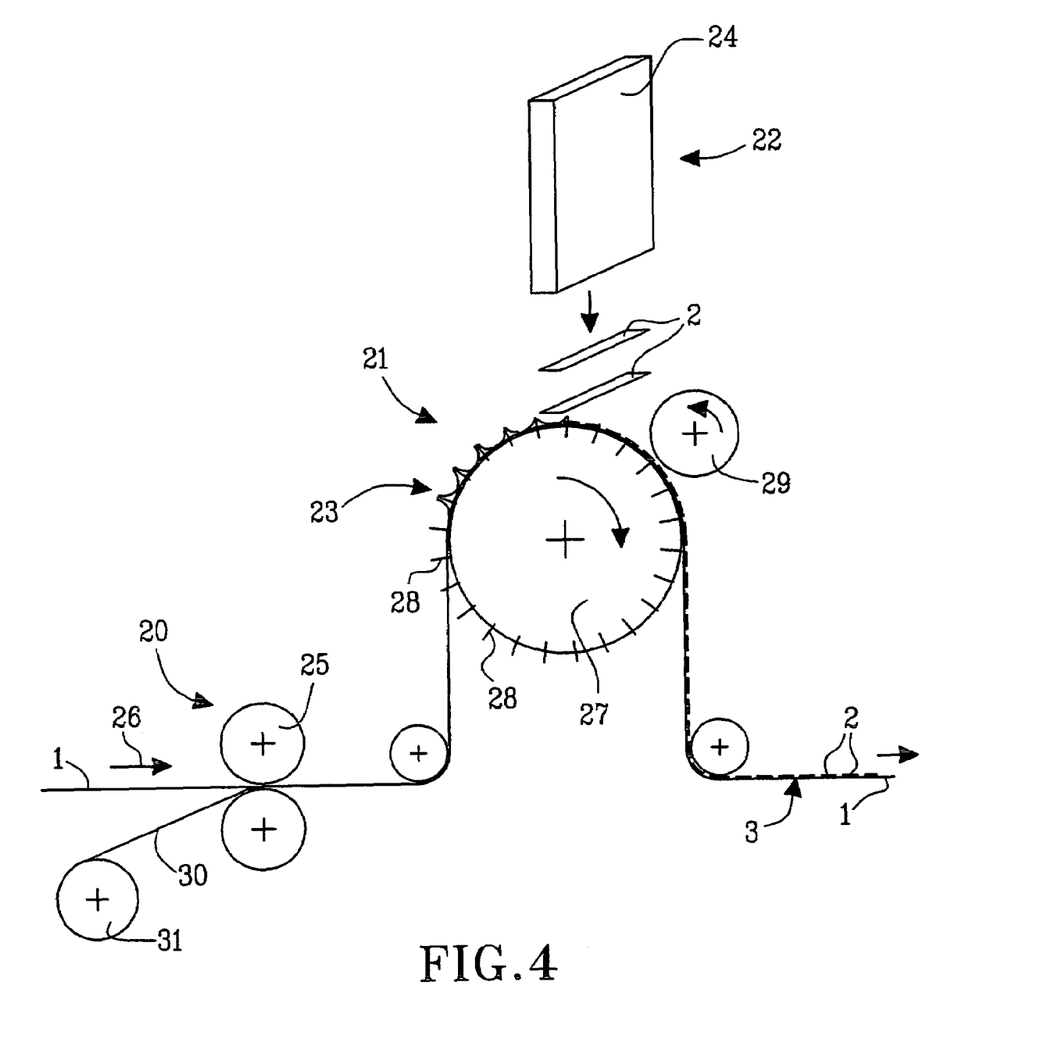

FIG. 4 is a schematic illustration of an embodiment of how the method according to the invention can be realized and, furthermore, of a device for manufacturing a layer 3 from a set of first strips 1 and a set of second strips 2. The device comprises a first unit 20 for feeding forward said first strips 1 in the form of continuous strips, and for forming cuts 4 in said first strips 1, to a means 21 for coupling together said first 1 and second strips 2, and a second unit 22 for providing said second strips 2 to the coupling means 21. Furthermore, the coupling means 21 comprises members 23 for preparing said first strips 1 for the application of said second strips 2 in the cuts 4 of said first strips 1.

The second unit 22 can be a storage 24 from which said second strips 2 can be provided. Of course, one or several storages, or another device having the corresponding function, can be used for providing said second strips, preferably piece by piece, to the coupling means 21. Instead, it is also possible to feed the second strips from one or several rolls, and to cut these strips into desired lengths in connection with the application of these on the first strips. In the illustrated example, the second strips 2 are placed so that said first 1 and second 2 strips cross each other, and preferably so that the first 1 and second 2 strips are arranged substantially perpendicularly in relation to each other. The first strips 1, which preferably are continuous strips, are fed forwards to the coupling means 21. Although different techniques for cutting, punching or shearing can be included for achieving the cuts 4 according to the invention, FIG. 4 shows a schematic illustration of an embodiment where a cutting roll 25, or so-called RDC-technique (Rotary Die Cutting), is used in order to provide the first strips 1 with the requisite cuts 4. Suitably, a plurality of said first strips 1, being arranged next to each other along a direction substantially perpendicular to the direction of feed 26, are fed forwards simultaneously, for example by means of one or several pairs of rolls 25, and thereby the strips are provided with requisite cuts 4 by means of said RDC-technique.

The length of the second strips 2 is adapted to the desired width of the formed layer 3. In the embodiment in which said second strips 2 are placed substantially perpendicularly in relation to the direction of feed 26 or, in other words, substantially in parallel with the longitudinal direction of the rolls, the length of said second strips 2 can be substantially equal to the distance between the two outermost first strips 1.

The coupling means 21 can include a roll 27 being provided with said members 23, such as spikes 28 protruding from the roll 27 or drum, for preparing the first strips 1, for example by means of turning up said flaps 11 being arranged on the first strips 1, so that the second strips 2 can be arranged in the cuts 4. Furthermore, a turning-down means, such as an additional roll 29, or a brush or the like, which is not necessarily rotatable but only abuts against the roll 27, can be arranged for turning the up-turned flaps 11 back down when the second strips 2 have been arranged in their intended positions. In such a case, the spikes 28 of the first roll 27 suitably exhibit the property that they can be folded aside or retracted into the roll 27 when said additional roll 29 turns the flaps 11 of the first strips 1 back down.

Before the first strips 1 are provided with cuts 4, if desired, the strips can be coated with an additional layer 30 of another material, such as a nonwoven, for example with the object of improving the tensile strength of the first strips 1 and, consequently, of the absorbent layer 3 and the absorbent body formed by the strips. The material for the additional layer can be delivered, for example, from a roll 31.

It is emphasized that the invention is not restricted to the embodiments of the invention described by way of example, but a plurality of variants and modifications of the invention within the scope of the subsequent claims and equivalents thereof will become evident to the skilled person once the inventive idea has been disclosed. For instance, the first strips could exhibit cuts having only one longitudinal direction of extension which is substantially parallel to the longitudinal direction of the first strips. The cuts could be of approximately the same length, or somewhat longer than the width of the second strips. Thereby, no real flap which can turned aside is created, but the coupling together of the strips and the forming of the absorbent layer would in this case take place by means of the second strips being inserted into these cuts.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent body comprising a set of first flat strips each having a plane and a set of second flat strips each having a plane, wherein said first and second strips are coupled to each other such that the planes of the first and second flat strips are parallel to each other and substantially adjacent to each other in order to form an absorbent layer of the body, said first and second flat strips are coupled to each other by said first flat strips being provided with cuts in which said second flat strips are arranged.

2. The absorbent body according to claim 1, wherein said cuts have an extension in a longitudinal direction which is substantially parallel to the longitudinal direction of said first strips.

3. The absorbent body according to claim 1, wherein said cuts have an extension in a longitudinal direction which is substantially perpendicular in relation to the longitudinal direction of said first strips.

4. The absorbent body according to claim 3, wherein a length of said cuts, with regard to the extension substantially perpendicularly in relation to the longitudinal direction of said first strips, corresponds to approximately half a width of one of said first strips.

5. The absorbent body according to claim 2, wherein a length of said cuts, with regard to the extension substantially in parallel with the longitudinal direction of said first strips, corresponds to approximately one width of one of said first strips.

6. An absorbent body comprising a set of first strips and a set of second strips, wherein said first and second strips are coupled to each other in order to form an absorbent layer of the body said first and second strips are coupled to each other by said first strips being provided with cuts in which said second strips are arranged, wherein said cuts are substantially L-shaped.

7. The absorbent body according to claim 1, wherein said cuts are arranged in order to form flaps in said first strips, wherein said flaps can be turned up or down in relation to said respective first strip for arranging one of said second strips between the respective flap and said first strip.

8. The absorbent body according to claim 7, wherein along the extension of said second strip in the longitudinal direction thereof, said second strip is arranged between a plurality of flaps and said first strips.

9. The absorbent body according to claim 8, wherein said flaps are arranged for locking said second strip in relation to said first strips in a first direction, being substantially parallel to the longitudinal direction of said first strips, and in a second, opposite direction.

10. The absorbent body according to claim 9, wherein the flaps are arranged alternatingly on said first strips so that, for a given flap, said second strip is locked in relation to said first strips in a direction parallel to the longitudinal direction of said first strips and, by means of the closest adjacent flap along said second strip, this is locked in the substantially opposite direction.

11. The absorbent body according to claim 7, wherein a portion of the periphery of the respective flap is formed by a portion of one of the longitudinal side edges of the respective first strip.

12. The absorbent body according to claim 1, wherein one of the cuts extends from a position at one of the longitudinal side edges of a respective first strip and further into the strip.

13. The absorbent body according to claim 1, wherein said second strips have cuts for receiving said first strips.

14. The absorbent body according to claim 1, wherein said first strips are arranged substantially in parallel with each other and said second strips are arranged substantially in parallel with each other.

15. The absorbent body according to claim 1, wherein said first strips are arranged substantially in parallel with each other or said second strips are arranged substantially in parallel with each other.

16. The absorbent body according to claim 1, wherein said first and second strips are arranged so that they cross each other.

17. The absorbent body according to claim 15, wherein said first and second strips are arranged substantially perpendicularly in relation to each other.

18. The absorbent body according to claim 1, wherein said first strips are arranged in order to partially overlap each other and that said second strips are arranged in order to partially overlap each other.

19. The absorbent body according to claim 1, wherein said first strips are arranged in order to partially overlap each other or that said second strips are arranged in order to partially overlap each other.

20. The absorbent body according to claim 1, wherein the body comprises at least two of said absorbent layers, which are arranged in a substantially parallel disposition in relation to each other and which overlap each other.

21. The absorbent body according to claim 18, wherein said absorbent layers are arranged alternatingly so that, for a given layer, said first strips have a longitudinal direction of extension being substantially perpendicular to the direction of extension of said first strips of the closest adjacent layer.

22. The absorbent body according to claim 1, wherein the material of said first strips and of said second strips is chosen from a group of fibrous materials, said group including cellulosic fibres, synthetic fibres such as thermoplastic fibres of polypropylene and polyethylene.

23. The absorbent body according to claim 1, wherein the material of said first strips or of said second strips is chosen from a group of fibrous materials, said group including cellulosic fibres, synthetic fibres such as thermoplastic fibres of polypropylene and polyethylene.

24. The absorbent body according to claim 1, wherein the material of said first strips and of said second strips is chosen from a group of non-fibrous materials, said group including foam-based materials and materials in the form of a film.

25. The absorbent body according to claim 1, wherein the material of said first strips or of said second strips is chosen from a group of non-fibrous materials, said group including foam-based materials and materials in the form of a film.

26. The absorbent body according to claim 1, wherein the material of said first strips and of said second strips is chosen from a group of absorbent materials, said group including cellulose pulp, superabsorbents, absorbent foams, and absorbent synthetic fibres.

27. The absorbent body according to claim 1, wherein the material of said first strips or of said second strips is chosen from a group of absorbent materials, said group including cellulose pulp, superabsorbents, absorbent foams, and absorbent synthetic fibres.

28. An absorbent product comprising a substantially fluid-impervious layer and a substantially fluid-pervious layer, wherein an absorbent body according to claim 1 is arranged between the fluid-impervious layer and the fluid-pervious layer.

29. A method for manufacturing an absorbent body, comprising:
coupling a set of first strips and a set of second strips to each other so that planes of the first strips are substantially parallel to and adjacent planes of the second strips to form an absorbent layer of the body,
providing said first strips with cuts in which said second strips are arranged.

30. The method according to claim 29, wherein designing said cuts so that flaps, which can be turned up or down in relation to said first strips, are formed in said first strips.

31. The method according to claim 29, wherein the cuts are substantially L-shaped cuts.

32. An absorbent body comprising:
a set of first strips, the first strips being provided with cuts extending from one or more longitudinal edges of each of the first strips toward a center of each of the first strips; and
a set of second strips, wherein the first and second strips are coupled to each other in order to form an absorbent layer of the body;
the second strips are arranged in the slits of the first strips in order to couple the first and second strips together in a substantially coplanar manner.

33. The absorbent body according to claim 32, wherein the cuts are arranged in order to form flaps in the first strips.

34. The absorbent body according to claim 33, wherein the flaps can be turned up or down in relation to the respective first strip for arranging one of the second strips between the respective flap and the first strip.

35. The absorbent body according to claim 33, wherein the cuts are either L-shaped or curved.

* * * * *